(12) United States Patent
Worthington et al.

(10) Patent No.: US 7,061,594 B2
(45) Date of Patent: Jun. 13, 2006

(54) DISC DRIVE SYSTEM AND METHODS FOR USE WITH BIO-DISCS

(75) Inventors: Mark Oscar Worthington, Irvine, CA (US); Kevin Robert McIntyre, Irvine, CA (US)

(73) Assignees: Burstein Technologies, Inc., Irvine, CA (US); Nagaoka & Co., Ltd., Hyogo (JP)

(*) Notice: Subject to any disclaimer, the term of this patent is extended or adjusted under 35 U.S.C. 154(b) by 760 days.

(21) Appl. No.: 10/008,156

(22) Filed: Nov. 9, 2001

(65) Prior Publication Data

US 2002/0122364 A1 Sep. 5, 2002

Related U.S. Application Data

(60) Provisional application No. 60/293,093, filed on May 22, 2001, provisional application No. 60/260,761, filed on Jan. 9, 2001, provisional application No. 60/247,465, filed on Nov. 9, 2000.

(51) Int. Cl.
*G01N 21/03* (2006.01)
*G11B 7/00* (2006.01)
*G01N 21/29* (2006.01)

(52) U.S. Cl. .................. 356/72; 356/73; 369/44.11; 369/53.1

(58) Field of Classification Search .............. 356/72, 356/73, 436, 445; 369/14, 44.11, 53.1, 53.2, 369/93
See application file for complete search history.

(56) References Cited

U.S. PATENT DOCUMENTS 3,901,658 A 8/1975 Burtis et al.
3,966,322 A 6/1976 Greaves et al.
4,469,793 A 9/1984 Guigan
4,672,600 A 6/1987 Balston et al.
4,866,688 A 9/1989 Ohtake et al.
4,876,557 A 10/1989 Yabe
4,972,404 A 11/1990 Yamaguchi et al.
5,119,363 A 6/1992 Satoh et al.
5,122,284 A 6/1992 Braynin et al.
5,130,963 A 7/1992 Kusano et al.
5,173,262 A 12/1992 Burtis et al.
5,310,523 A 5/1994 Smethers et al.
5,329,461 A 7/1994 Allen et al.
5,407,554 A 4/1995 Saurer
5,412,087 A 5/1995 McGall et al.
5,457,053 A 10/1995 Burd et al.
5,506,827 A 4/1996 Tobita
5,508,985 A 4/1996 Fairchild et al.
5,510,270 A 4/1996 Fodor et al.
5,513,169 A 4/1996 Fite et al.
5,572,507 A 11/1996 Ozaki et al.
5,585,069 A 12/1996 Zanzucchi et al.
5,629,514 A 5/1997 Lee et al.

(Continued)

FOREIGN PATENT DOCUMENTS

EP 0 392 475 A2 10/1990

(Continued)

*Primary Examiner*—Layla G. Lauchman
(74) *Attorney, Agent, or Firm*—Knobbe, Martens, Olson & Bear, LLP

(57) ABSTRACT

An optical disc drive for reading encoded information, such as on a CD, CD-R, or DVD, is modified to read biological or chemical investigational features from a disc. The modifications can include software changes or the addition of hardware desirably without the need to modify the disc drive electronics.

12 Claims, 9 Drawing Sheets

U.S. PATENT DOCUMENTS

| | | | |
|---|---|---|---|
| 5,631,844 A | 5/1997 | Margrey et al. | |
| 5,661,703 A | 8/1997 | Moribe et al. | |
| 5,671,202 A | 9/1997 | Brownstein et al. | |
| 5,696,757 A | 12/1997 | Ozaki et al. | |
| 5,737,478 A | 4/1998 | Yamagishi et al. | |
| 5,768,227 A | 6/1998 | Baba | |
| 5,793,969 A | 8/1998 | Kamentsky et al. | |
| 5,834,758 A | 11/1998 | Trulson et al. | |
| 5,837,552 A | 11/1998 | Cotton et al. | |
| 5,863,708 A | 1/1999 | Zanzucchi et al. | |
| 5,878,018 A | 3/1999 | Moriya et al. | |
| 5,879,774 A | 3/1999 | Taylor et al. | |
| 5,882,903 A | 3/1999 | Andrevski et al. | |
| 5,892,577 A * | 4/1999 | Gordon | 356/73 |
| 5,922,617 A | 7/1999 | Wang et al. | |
| 5,994,150 A | 11/1999 | Challener et al. | |
| 6,009,057 A | 12/1999 | Furukawa et al. | |
| 6,013,352 A | 1/2000 | Gallant | |
| 6,030,581 A | 2/2000 | Virtanen | |
| 6,031,815 A | 2/2000 | Heemskerk | |
| 6,121,048 A | 9/2000 | Zaffaroni et al. | |
| 6,147,941 A | 11/2000 | Kumagai | |
| 6,212,158 B1 | 4/2001 | Ha et al. | |
| 6,231,812 B1 | 5/2001 | Rothberg et al. | |
| 6,233,207 B1 | 5/2001 | Tanaka | |
| 6,256,088 B1 * | 7/2001 | Gordon | 356/73 |
| 6,327,031 B1 * | 12/2001 | Gordon | 356/72 |
| 6,339,473 B1 * | 1/2002 | Gordon | 356/440 |
| 6,342,395 B1 | 1/2002 | Hammock et al. | |
| 6,395,562 B1 * | 5/2002 | Hammock et al. | 436/518 |
| 6,438,097 B1 | 8/2002 | Kajiyama et al. | |
| 6,476,907 B1 * | 11/2002 | Gordon | 356/73 |
| 6,646,967 B1 | 11/2003 | Garcia | |
| 6,760,298 B1 | 7/2004 | Worthington et al. | |
| 6,813,237 B1 | 11/2004 | Yamaguchi et al. | |
| 6,920,092 B1 * | 7/2005 | Kuriuzawa et al. | 369/44.28 |
| 2002/0047003 A1 | 4/2002 | Bedingham et al. | |
| 2002/0076354 A1 | 6/2002 | Cohen | |
| 2002/0097658 A1 | 7/2002 | Worthington et al. | |
| 2002/0098528 A1 | 7/2002 | Gordon et al. | |
| 2002/0145960 A1 | 10/2002 | Worthington et al. | |
| 2002/0168652 A1 | 11/2002 | Werner et al. | |
| 2002/0168663 A1 | 11/2002 | Phan et al. | |
| 2002/0171838 A1 | 11/2002 | Pal et al. | |
| 2003/0104486 A1 | 6/2003 | Selvan | |

FOREIGN PATENT DOCUMENTS

| | | |
|---|---|---|
| EP | 0 417 305 A1 | 3/1991 |
| EP | 0 521 421 A2 | 1/1993 |
| EP | 0 866 449 A2 | 3/1998 |
| GB | 2 337 113 A | 11/1999 |
| WO | WO 96/09548 | 3/1996 |
| WO | WO 98/01857 | 1/1998 |
| WO | WO 98/12559 | 3/1998 |
| WO | WO 98/38510 | 9/1998 |
| WO | WO 00/05582 | 2/2000 |
| WO | WO 00/26677 | 5/2000 |

* cited by examiner

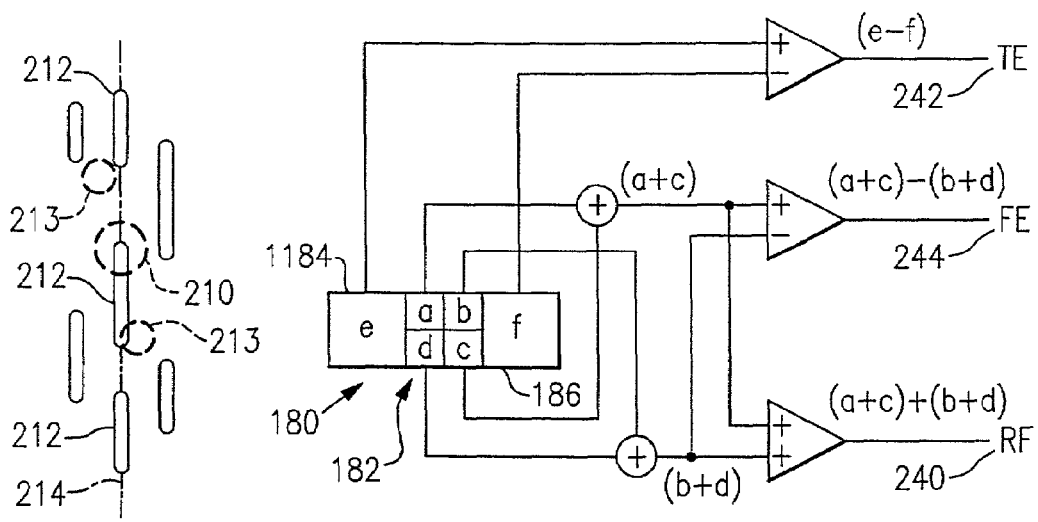
FIG.5
Prior Art
FIG.4
Prior Art
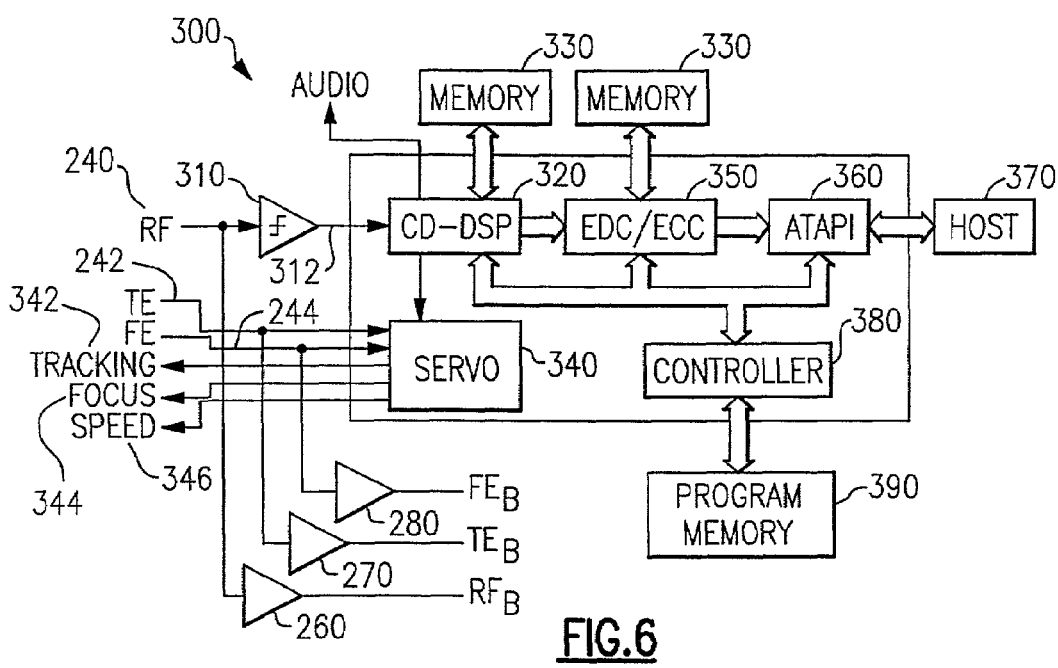
FIG.6

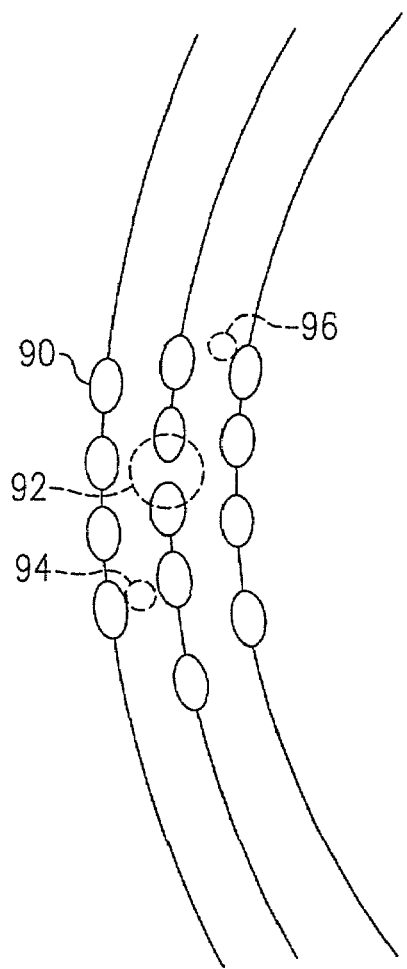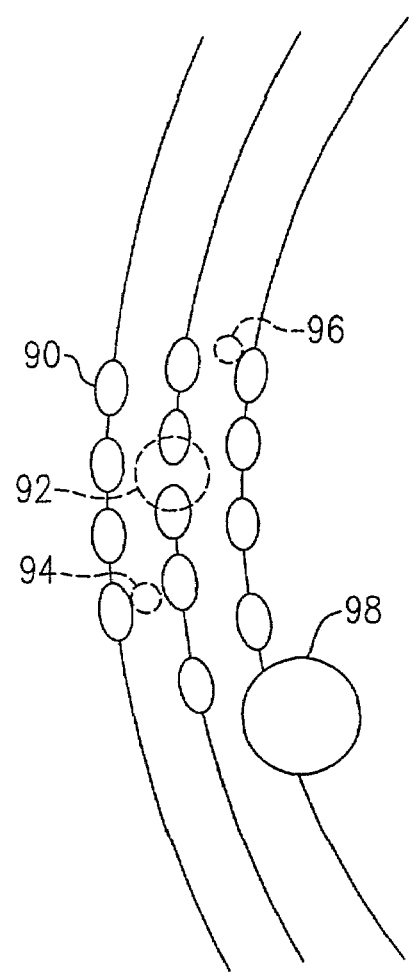
FIG.11
Prior Art
FIG.12

DISC DRIVE SYSTEM AND METHODS FOR USE WITH BIO-DISCS

CROSS-REFERENCE TO RELATED APPLICATIONS

This application claims priority from U.S. provisional applications 60/247,465, filed Nov. 9, 2000; 60/260,761, filed Jan. 9, 2001; and 60/293,093, filed May 22, 2001. Each of these priority documents is expressly incorporated herein by reference.

BACKGROUND OF THE INVENTION

The present invention relates to the use of optical discs and optical disc readers for performing assays.

Commonly assigned, U.S. patent applications Ser. No. 09/183,842, filed Oct. 30, 1998; Ser. No. 09/311,329, filed May 11, 1999; and Ser. No. 09/421,870, filed Oct. 26, 1999, are each hereby incorporated by. reference. These applications describe methods and apparatus for detecting operational structures, such as pits or dye regions, and investigational features, such as biological material, on one or more surfaces of an optical disc assembly.

Deriving information about operational structures and investigational features using a single optical path may require complex manipulation of the information processed in the optical path, as discussed, for example, in copending commonly-assigned U.S. patent application Ser. No. 09/378, 878, which is hereby incorporated by reference in its entirety.

SUMMARY OF THE INVENTION

The present invention provides methods and apparatus for detecting investigational features on an optical disc. The structures, features, characteristics, and attributes which can be investigated according to the present invention with investigational features may include biological, chemical, or organic specimens, test samples, investigational objects such as organic material, and similar test objects or target samples. Such structures, features, and attributes may be imaged on an output monitor. The investigational features may also include specific chemical reactions and the products and by-products resulting therefrom, such as, any one of a variety of different colorimetric assays. These features can be used for medical assays, but also for other uses, such as to detect chemicals or detect water purity.

An optical bio-disc may be implemented on an optical disc including a format such as CD, CD-R, CD-RW, DVD, DVD-R, DVD-RW, or a modified version thereof. The bio-disc may include encoded information for performing, controlling, and post-processing the test or assay. For example, such encoded information may be directed to controlling the rotation rate of the disc. Depending on the test, assay, or investigational protocol, the rotation rate may be variable with intervening or consecutive sessions of acceleration, constant speed, and deceleration. These sessions may be closely controlled both as to speed and time of rotation to provide, for example, mixing, agitation, or separation of fluids and suspensions with agents, reagents or antibodies. A disc drive assembly is employed to rotate the disc, read and process any encoded information stored on the disc, and analyze the liquid, chemical, biological, or bio-chemical component or other investigational feature in an assay zone of the disc. The disc drive assembly may also be utilized to write information to the bio-disc either before or after the material in the assay zone is analyzed by the read beam of the drive.

In one embodiment, one or more signal processing circuits within an optical disc drive are programmably configured to function as an analog to digital converter (ADC), and preferably to bypass demodulator and error correction circuitry. The ADC is used to detect an electronic profile associated with investigational features on or in the optical disc. The profiles may be used to determine relative size, composition, and location of the detected structures. The disc drive may optionally be programmably returned to its standard operating configuration. The ADC functionality may be incorporated in a digital signal processor (DSP) which is programmable without hardware change. The programming may cause the signal from the ADC to be provided to an output lead of the DSP, or the programming could cause the signal to essentially pass through other components from the ADC without being substantially altered.

The present application relates to other ways in which a conventional optical disc drive having a light source, a detector for detecting light reflected from the light source to the disc, and various signal processing circuitry may be used to obtain information about an investigational feature.

In another embodiment, the disc is made using a semi-reflective (and semi-transparent) material such that light can be reflected and detected by the disc drives normal detector. Additional functionality can be provided over the disc to detect transmitted light. These additional components can use a detector with one or more detecting elements, a pre-amplifier, automatic gain control, an analog switch for combining signals from multiple elements (if provided), and additional processing circuitry including an ADC, microprocessor, and/or threshold detector and event counter. These items are preferably provided on a board that can be added to the device through retro-fitting such that a conventional, commercial disc drive, preferably of the type that can be provided into a compartment of a personal computer is modified without changing the basic functionality of the disc drive. In the preferred embodiment, no wires need be attached to the reflective light source, detector, or processing circuitry, although some connections could be made if desired, for example, to compare signals received by the top and bottom detectors.

In the case of the semi-reflective, semi-transparent disc, the encoded information is provided as it conventionally is in a CD, CD/R, or DVD, while investigational features are provided at target zones where the encoded information is removed, allowing more transmission with less reflection. The system preferably includes a form of triggering that can either be hardware or software based. A triggering signal indicates that an investigational feature is being observed. This can arise from a physical trigger mark located on the disc that identifies a radius along which there are target zones with investigational features, or it can include encoded data identifying where a target zone is located. In the case of a hardware trigger, the signal from the triggering sensor can be provided to an ADC or other processing circuitry that causes that circuitry to process the current detector signal; in the case of software triggering, the software controls the ADC or other processing circuitry. The data collected under software control is subsequently searched through for the software trigger data pattern. This pattern identifies the location in the data of the investigational features.

In other embodiments for using and modifying a conventional disc drive, additional firmware modifications may be made to the disc drive. In many cases, such firmware changes are ones that are known in the field of disc analysis and/or drive analysis, but are not used in conventional disc drive systems and would generally be considered unnecessary or even undesirable. For example, for analysis purposes one may want to look at errors that are generated, automatic gain control values, laser power values, laser monitor values, and many other parameters relating to the reading of a disc by a drive. In typical conventional disc drives, however, a user, such as a consumer, would typically want to use a disc that plays music or provides data, without setting parameters. Consequently, conventional systems generally have no need or desire for monitoring or controlling such other parameters. According to embodiments of the present invention, firmware changes that are useful in a disc drive system for detecting investigational features may be made. For example, in a disc in which a fluid is provided into a channel to be moved along the channel in response to rotation, and detected by the laser/detector in a drive, it may be desirable to be able to control the rotation rate of the disc when it begins, and also to control the laser power, to avoid unwanted movement or heating.

Another use of such firmware changes can be to monitor a parameter that indicates some useful information about an investigational feature. For example, automatic gain control can be provided so that the detector output signal is amplified by a variable amount. The amount of gain is inversely related to the amount of light falling on the detector. In a conventional disc, the device is only reading binary data (0 or 1), but an investigational feature may require data to be read over a continuum of values. The level of gain may serve as an indicator of the investigational feature—the larger the gain the smaller the, and vice versa. The automatic gain control value can thus be used to image, detect, or assess the investigational feature.

While several firmware changes have been mentioned here, the embodiments below indicate a number of other features that are useful modifications to a conventional drive. By making these changes in firmware. the drive capabilities can be modified in some respects and yet use conventional hardware is modified.

According to yet another embodiment of the invention, multiple optical paths are provided, such that various functions of an optical disc system can be isolated and optimized. For example, an optical disc system performs a number of functions, including tracking, focusing, and synchronizing. When each of these functions manipulates a single signal (e.g., a quad-sum signal), these functions are said to be linked. The linking of individual functions can be problematic because the optimal system settings for performing each of these functions may be different. For example, in a pits and lands type of optical disc, the optimal pit depth for retrieving tracking information is ⅛ the wavelength of the light beam used by the system. In contrast, the optimal pit depth for retrieving synchronization information is ¼ the light beam wavelength. Because only one signal is being used for both tracking and synchronization, this difference requires that a pit depth be chosen that optimizes neither the tracking nor the synchronization functions.

When multiple paths are used to create distinct signals, the tracking signal can be isolated from the synchronization signal and each set of pits can be formed to meet the optimal requirements for each function. Thus, for example, the pits used for tracking can be formed with a depth of ⅛ the light wavelength that is used to read the signal, and the pits used for synchronization can be formed to be ¼ the light wavelength that is used to read the signal.

In an illustrative optical disc system according to the invention, one signal can be generated to detect the standard optical disc operational information, such as tracking, focus, and synchronization, while another signal can be generated to detect investigational features or structures disposed on the same or different surface of the disc assembly. Thus, the system can separately detect operational data and investigational features located on one or more surfaces of an optical disc assembly.

One method of producing multiple optical paths for detecting operational structures and investigational features is by using a "three-beam" optical design. In a conventional three-beam design, for example, a quadsum detector is used for focus and synchronization functions. The tracking functions, which can be performed by two additional signal detectors, known commonly as "outriggers," are fixed on either side of the quad-sum detector. Thus, two distinct photometric arrays are provided for detecting signals from the optical disc assembly. As used herein, a photodiode array is a set of one or more photo-detector elements.

One method of generating multiple coherent or non-coherent light beams (e.g., three beams for the three-beam system) is by passing the light through a diffraction grating, which can be a screen with slits spaced only a few light wavelengths apart. A one-beam pickup accomplishes all of these tasks with one beam.

In a system according to the invention, which uses a multiple-beam pick-up, one beam may also be used to provide all the tasks of a typical optical system and the additional beams may be used to detect investigational features or structures on the optical disc assembly concurrently or nonconcurrently.

These and other advantages will become apparent from the following detailed description taken in conjunction with the accompanying drawing figures and claims.

BRIEF DESCRIPTION OF THE DRAWINGS

FIG. 4 is an exemplary optical disc detector and associated electronics that use three beams for tracking, focusing, and reading.

FIG. 5 shows the position of beams from a typical three-beam pickup relative to a track on an optical disc.

FIG. 6 is a block diagram of a chip set of a generic optical disc reader, modified to monitor signals for determining the presence of investigational features or structures on an optical disc.

FIG. 11 is a prior art view showing a three-beam system projecting onto three tracks of the disc.

FIG. 12 is a top view of three beams on three tracks, one of which has an investigational feature.

DETAILED DESCRIPTION

Figure 1:
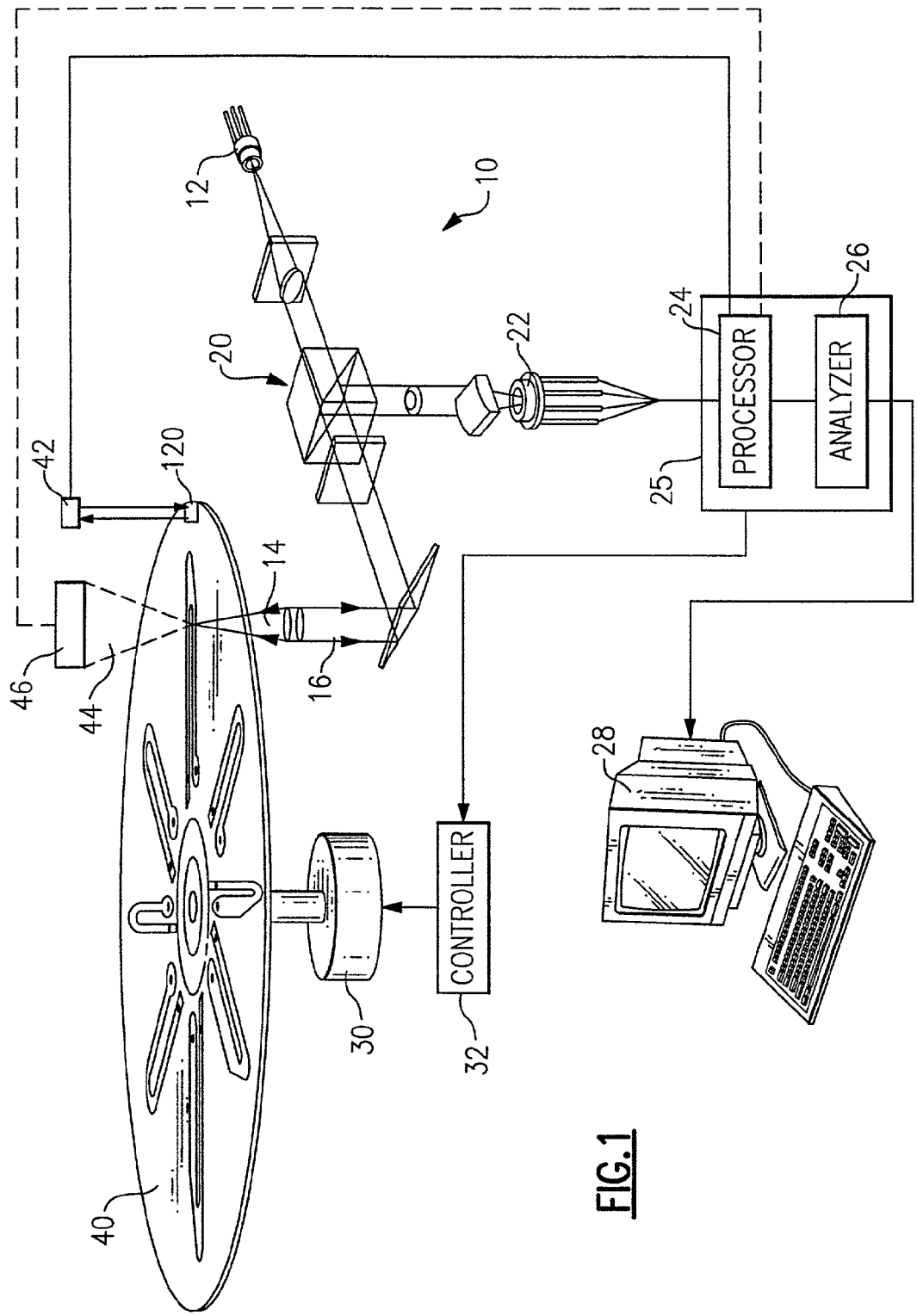
FIG. 1 is a perspective view and block diagram of a disc and disc reading system.

FIG. 1 shows an optical disc reader system 10. This system may be a conventional reader for CD, CD-R, DVD, or other known comparable format, a modified version thereof, or a distinct dedicated device. The basic components of an optical reading system are a light system for providing light, motors for rotating the disc and moving the light system, and a detection system for detecting light and processing signals.

A light source 12 provides light to optical components 20 to produce an incident light beam 14, and a return beam 16. In the case of a reflective disc or portion of a disc, return beam 16 is reflected from a reflective surface. Return beam 16 is provided back to optical components 20, and then to a bottom detector 22. Optical components 20 can include a lens, a beam splitter, and a quarter wave plate that changes the polarization of the light beam so that the beam splitter directs a reflected beam through the lens to focus the reflected beam onto the detector. An astigmatic element, such as a cylindrical lens, may be provided between the beam splitter and detector to introduce astigmatism in the reflected light beam.

Data from detector 22 is provided to a computer 25 with a processor 24 and an analyzer 26 to provide an image to a monitor 28. The computer can represent a desktop computer, programmable logic, or some other processing device, and also can include a connection (such as over the Internet) to other processing and/or storage devices. A drive motor 30 and a controller 32 are provided for controlling the rotation of disc 40. Methods and systems for reading such a disc are also shown in the incorporated U.S. Pat. No. 5,892,577. A hardware trigger sensor 42 may be used. Triggering sensor 42 provides a signal to processor 24 that allows for the collection of data by processor 24 only when incident beam 14 is on a target zone. In this case, data is not collected when the trigger is not detected. The trigger is preferably aligned radially with target zones. Trigger sensor 42 may be located on the bottom side of the disk 40.

The system may also include a top detector 46 for detecting transmitted light 44. This light could pass through a semi-reflective disc, or through a portion where portions of the disc have been removed.

The disc drive assembly is thus employed to rotate disc 40, read and process any encoded operational information stored on the disc, analyze the liquid, chemical, biological, or biochemical investigational features in an assay region of the disc, to write information to the disc either before or after the material in the assay zone is analyzed by the read beam of the drive. Other than the trigger sensor and the transmissive detector, the remaining components are parts of generally known optical disc readers, and the incorporated '577 patent shows the use of a separate top detector and bottom detector.

Figure 2:
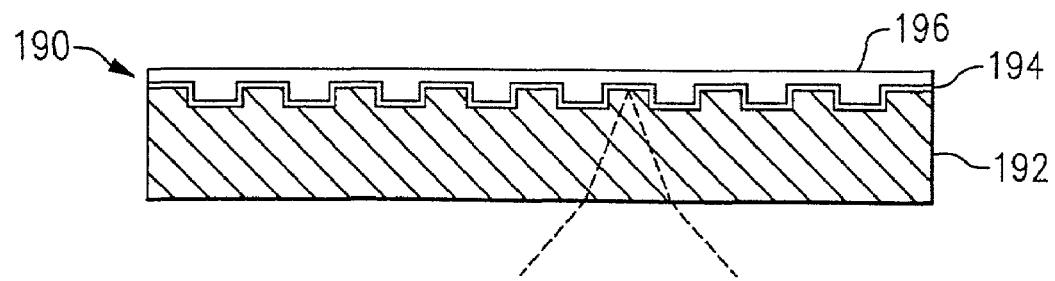
FIG. 2 is a side cross-sectional view of a disc.

Referring to FIG. 2, disc 190 has layers from light-proximal to light-distal, including transmissive substrate 192 (such as 1.2 mm polycarbonate), reflective layer 194 (such as a gold or aluminum layer), and a protective cap layer 196. Transparent substrate 192 makes up most of the thickness of a typical CD-type disc, as measured along the optical axis, and provides both optical and structural features necessary for disc operation.

Substrate layer 192 is typically impressed with a spiral track that starts at the innermost readable portion of the disc and then spirals out to the outermost readable portion of the disc. In a non-recordable typical CD disc, this track is made up of a series of embossed pits, each typically having a depth of approximately one-quarter the wavelength of the light that is used to read the disc. The pits have varying lengths. The length and spacing of the pits encode operational data.

Figure 3:
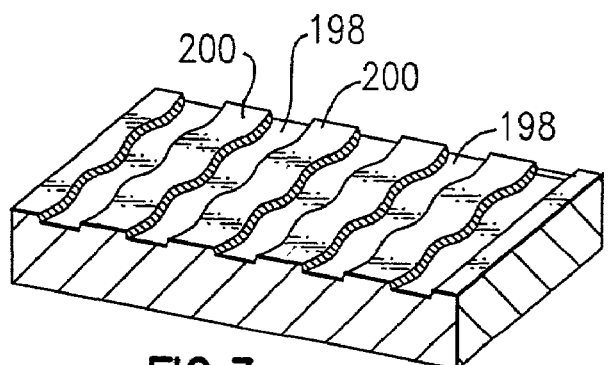
FIG. 3 is a perspective view of a surface of a CD-R disc with wobble grooves.

The spiral groove of a recordable disc, such as CD-R has a wobble groove rather than pits. FIG. 3 shows two portions of such a wobble groove, i.e., an embossed portion 200 and a groove portion 198.

Referring to FIG. 4, an exemplary detector 180 and its associated electronics are described in more detail. Detector 180 typically includes a central detector 182, and can be bordered by additional detector elements 184 and 186. Central detector 182 may be split into multiple detector elements, e.g., four, represented as a, b, c, and d. Detector elements a, b, c, and d (sometimes collectively referred to as a "quad detector") each provide electrical signal indicative of the intensity of the reflected light beam striking that element.

The sum of the signals from center detector 182 (i.e., a+b+c+d) provides a radio frequency (RF) signal 240, also referred to as a high frequency (HF), quad-sum, or sum signal. As used herein the notation "a+b" indicates the sum of the signals from detector elements a and b. The RF signal is typically demodulated to recover data recorded on the optical disc.

Various pairs of the signals from detector elements a through f are also combined to provide feedback signals for tracking and focus control. For example, a tracking (tracking error, or TE) signal 242 may be obtained from the difference between the e and f signals (i.e., e−f). A focus error (FE) signal 244 may be obtained from the difference between the (a+c) and (b+d) signals.

The circuitry of FIG. 4 is just one example of circuitry that provides focus and tracking error signals in an optical disc player. Numerous methods are known for providing these signals. For example, a focus error signal may be obtained by the critical angle method, described in U.S. Pat. No. 5,629,514, or by Foucault and astigmatism methods, described in *The Compact Disc Handbook* by Pohlmann, A-R Editions, Inc. (1992), which are incorporated herein by reference. Similarly, tracking error signals may be obtained using a single beam push-pull or a three beam method described in *The Compact Disc Handbook*, a differential phase method described in U.S. Pat. No. 5,130,963, which is incorporated herein by reference, or a single beam high frequency wobble method.

Referring to FIG. 5, a CD drive typically uses a three-beam pickup, in which the light beam is split into three beams, a main beam and two tracking beams. The main beam is focused onto the surface of an optical disc so that it is centered on a tracking structure, whereas the tracking beams fall on the opposite sides of the tracking structure. Main beam 210 is shown centered on track 214 (as defined by pits 212), and tracking beams 213 falling on opposite sides of track 214. By design, the three beams are reflected from the optical disc and directed to detector 180 (FIG. 4) such that main beam 210 falls on the quad detector, and tracking beams 213 fall on sensor elements e and f. Typically, such processing is performed by analog circuitry in combination with one or more integrated circuit chips. Often, the circuitry takes the form of a special chip set or a single ASIC (application-specific integrated circuit) chip.

FIG. 6 is generalized block diagram including an illustrative chip set 300 for a typical optical drive system. Although the chip sets for CD, CD-R, and DVD drives can be somewhat different from one another, it will be understood that the system shown in FIG. 6 is meant to generically represent all types of optical drives.

RF signal 240, obtained from summing the signals from detector elements a, b, c, and d, is normally processed to extract whatever data is recorded on the optical disc. First, analog RF signal 240 is conditioned, with normalization and equalization performed. Next, RF analog signal 240 is converted to a digital signal comprising a serial stream of digital data referred to as channel bits. The channel bit stream is then demodulated according to the modulation standard used for the type of optical disc being read. For example, it is common for CD-type discs to use eight-to-fourteen (also denominated "eight-of-fourteen") modulation (EFM) wherein a data byte, or eight data bits, are encoded in fourteen channel bits. There are three merging bits between each group of fourteen channel bits. Thus, when reading a CD-type optical disc, seventeen channel bits are read from the optical disc, the merging bits are discarded, and the remaining fourteen bits are decoded, or demodulated, to obtain the original data byte. The data bytes themselves are grouped into blocks, which are further processed to reduce the effects of disc defects, such as scratches on the disc surface.

RF signal 240 from detector 180 may be converted to a square wave signal 312 by a comparator 310, which provides a high output when RF signal 240 is above a threshold level, and a low output when RF signal is below the threshold. Digital signal processing circuit (DSP) 320 then samples square wave signal 312 to determine the value of each channel bit. DSP 320 further demodulates the channel bits to extract the data bytes which are then grouped into blocks and processed to detect and correct errors that may have occurred. Memory 330 provides temporary storage for the data as it is being processed by DSP 320 and assembled into blocks.

Servo block 340 analyzes tracking error (TE) signal 242 (or a wobble tracking error (WTE) in a DVD or CD-R system) and provides a tracking control signal 342 to the tracking mechanisms to ensure the pickup assembly maintains proper tracking. Similarly, a focus control signal 344 is provided based on focus error signal FE 244. DSP 320 provides an indication of the data rate of RF signal 240 which is used by servo block 340 to provide a speed control signal 346 to the spindle motor (not shown) of the optical disc drive.

In an audio CD player, after processing by DSP 320, each data block is sent to audio reproduction circuitry (not shown). However, in some data storage applications, each data block may contain additional error detection codes (EDC) and error correction codes (ECC). EDC/ECC circuitry 350 typically uses the EDC and ECC codes to increase the integrity of the data block by detecting and correcting errors not already corrected by DSP 320. Memory 332, which may be combined with memory 330, provides temporary storage for data blocks being processed by EDC/ECC circuitry 350. The data blocks are transferred from the optical disc player to a host 370 by means of interface circuitry 360. An ATAPI interface is shown, but it should be understood that other interfaces, such as SCSI, Firewire, or Universal Serial Bus (USB), and the like could also be used.

Controller 380 coordinates the operation of the various components of chip set 300, for example by coordinating the transfer of data blocks between DSP 320 and EDC/ECC circuitry 350. Controller 380 also keeps track of which data block is being read and may keep track of various parameters indicative of the operational status of the optical disc reader.

Program memory 390 has program code for the operation of controller 380. In many optical disc reader chip sets, program memory 390 may also contain program instructions for DSP 320 or EDC/ECC circuitry 350. This is advantageous for manufacturers in that the operation of the disc drive may be changed by altering the program code in program memory 390. For example, a newly developed method of modulating or encoding data on an optical disc may be accommodated by changing program memory 390.

While the foregoing description is sufficient for a basic understanding of the present invention, there are numerous alternative designs and configurations of an optical pickup and associated electronics which may be used in the context of the present invention. Further details and alternative designs are described in *Compact Disc Technology*, by Nakajima and Ogawa, IOS Press, Inc. (1992); *The Compact Disc Handbook, Digital Audio and Compact Disc Technology*, by Baert et al. (eds.), Books Britain (1995); *CD-Rom Professional's CD-Recordable Handbook: The Complete Guide to Practical Desktop CD*, Starrett et al. (eds.), ISBN: 0910965188 (1996); which are incorporated herein in their entirety by this reference.

To this point, the circuitry of FIG. 6 is known in prior optical disc drives. Chip set 300 can be modified from its original configuration by the addition of tap buffers 260, 270, and 280. These tap buffers provide access to unprocessed analog signals such as RF signal 240, TE signal 242, and FE signal 244, respectively, produced by detector 180, thereby permitting external instrumentation to receive these signals without interfering with normal drive operation.

An alternative modification is the addition of tap buffers to allow the unprocessed a though f signal from detector 180 to be processed by external instrumentation or additional circuitry. From these signals, the HF, TE, FE, or any other combination can be formed. Also, any additional detectors available can provide useful signals in this same manner (e.g., g and h detectors in current state-of-the-art drives). certain drive circuit designs and detector/amplifier devices allow connection of the instrumentation or additional circuitry directly to the detector without the need for the tap buffers.

The U.S. patent applications incorporated in the background section, including Ser. No. 09/183,842 (hereinafter the '842 application) discloses coupling an oscilloscope to RF signal 240 for detecting dual peak profiles associated with nonoperational structures or investigational features while acquiring the information needed to operate the disc drive. These peaks appear as a result of changes in reflectance as the light beam traverses investigational features on the optical disc surface. Such unique electronic profiles may be advantageously used to detect and discriminate among investigational features. An external analog to digital converter (ADC) may be connected to RF signal 240, for example, in order to determine the number of unique electronic peaks encountered (and thus the number investigational features) on any portion of the optical disc. The magnitude and/or duration of the digitized unique electronic profiles may be interpreted by an associated application program to determine the relative size, composition, and location of the detected structures.

Figure 7:
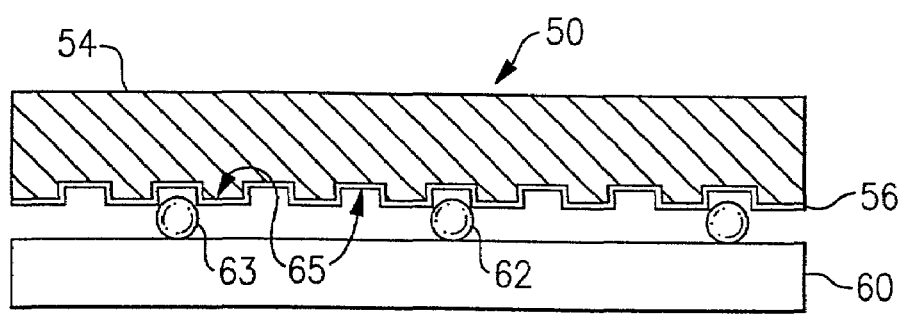
FIG. 7 illustrates a cross sectional side of a suitable disc assembly, including a light-refractive cover, for use with the present invention.

The '842 application teaches that micron-sized investigational features may be disposed upon a surface of an optical disc in a number of ways. One suitable embodiment for accomplishing this is depicted in FIG. 7. As shown in FIG. 7, light beam 50 is incident on the disc assembly from below. Disc 52 has disc substrate 54 and reflective layer 56, upon which investigational features 136 are disposed. Wobble groove 58, impressed in substrate 54 and coated by reflective layer 56, is indicated. Also shown is a nonintegral cover 60.

Investigational features 62 may be detected, measured, and characterized if reflective layer 56 is not fully reflective. The operational structures of the disc, including tracking features, may be detected concurrently (or nonconcurrently) with and readily discriminated from investigational features using a single optical pickup.

Investigational feature 63 is shown in a target zone in which the reflective layer is removed, thereby allowing light to be transmitted more easily without a reflective or semi-reflective layer. The disc can have a number of target zones 65, and these are preferably aligned along radii of the disc.

The material applied to the disc for investigation and analysis may include biological particulate suspensions and organic material such as blood, urine, saliva, amniotic fluid, skin cells, cerebrospinal fluid, serum. synovial fluid, semen, single-strand and double-strand DNA. pleural fluid, cells from selected body organs or tissue, pericardial fluid, feces, perintoneal fluid, and calculi. In the case of some of these materials, a reporter may be employed for detection purposes. These reporters include plastic micro-spheres or beads made of, for example, latex or polystyrene and colloidal gold particles with coatings of bio-molecules that have an affinity for a given material such as a biotine molecule in a strand of DNA. Appropriate coatings include those made from streptavidin or neutravidin, for example. In this manner, objects to small to be detected by the read beam of the drive, may still be detected by association with the reporter.

To acquire information concerning the investigational features, a standard suitable detection circuit can be coupled to the unprocessed RF signal. The type of signal processing performed by DSP 320, which typically includes demodulation, decoding, and error checking, is intended to convert EFM-encoded information on the RF signal to a specific digital format. RF signals processed in this manner may be less desirable for detecting the dual peaks associated with investigational features.

Figure 8:
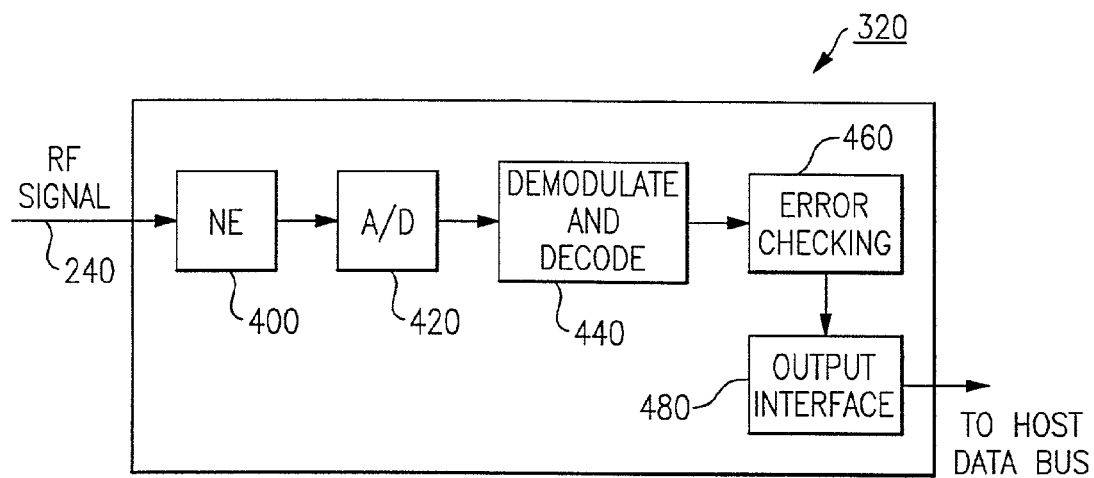
FIG. 8 is a functional block diagram of a conventional CD digital signal processing circuit.

FIG. 8 is a functional block diagram illustrating the signal processing that occurs within DSP 320 when configured in a conventional manner. As shown, DSP 320: (1) equalizes and/or normalizes the RF signal (block 400); (2) converts the normalized RF signal from the analog to digital (block 420); (3) demodulates and decodes the resulting EFM signal (block 440); (4) performs an error checking procedure (e.g., using Cross-Interleaved Reed-Solomon Code "CIRC" block 460); and (5) provides the resulting signal to an output interface for communication with host data bus (block 480). Examples of commonly used DSP chips that perform some or all of these functions include the SAA 7210, SAA 7220, and the SAA 7735, available from Philips Electronics Corporation, Eindhoven, Netherlands.

In accordance with one embodiment of the present invention, chip set 300 is reconfigured and/or reprogrammed so that physical modification of the optical disc drive is not necessary. One way this may be accomplished is by programming DSP 320 to operate simply as an A/D converter, and bypassing other functionality, such as the demodulator and decoder functionalities. In such a configuration, DSP chip 320 takes the place of an external A/D converter and effectively shunts the digitized RF signals directly to host data bus 370.

Investigational features may be detected by analyzing the resulting digitized RF signal. Alternatively, investigational features could be detected by routing an unprocessed RF signal through the chip set to an output terminal of the disc drive, connecting the signal to a personal computer, and using hardware and software within the personal computer to perform the A/D conversion and analysis.

DSP 320 can be programmably configured as an A/D converter without additional demodulation and error correction in multiple ways. For example, a configuration routine stored in program memory 390 may operate via controller 380 to reconfigure DSP 320. Alternatively, an application program may be used to selectively reconfigure DSP 320 through interface circuitry 360 as required. DSP 320 may also configure itself as an AND converter when it receives a certain type of RF signal, or from other information read from the disc. These methods are merely illustrative, and any other suitable software or firmware based reconfiguration method or path may be used if desired.

Figure 9:
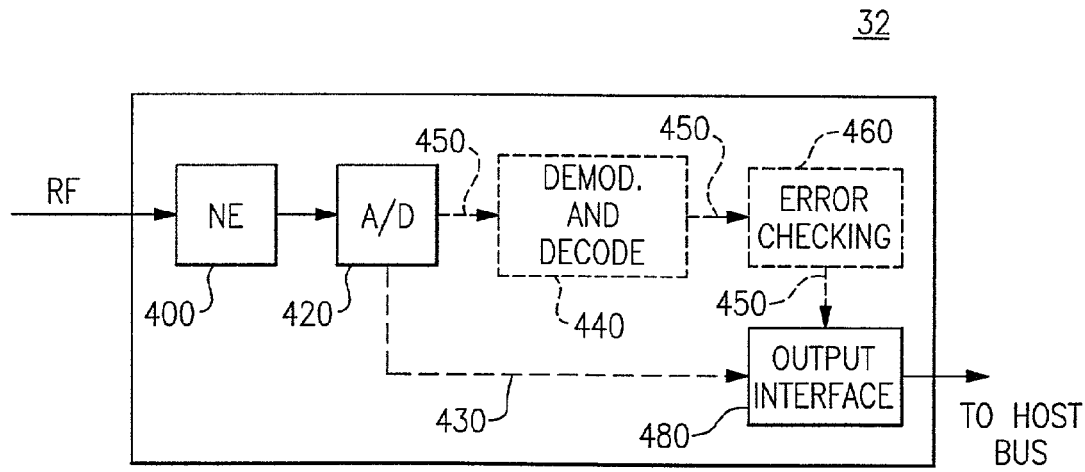
FIG. 9 is a functional block diagram of a digital signal processing circuit programmably configured as an analog to digital converter in accordance with the principles of the present invention.

FIG. 9 shows a block diagram illustrating some of the ways in which the processing resources within DSP 320 may be reconfigured to produce a suitable A/D converter. In one arrangement, A/D block 420 is disconnected from paths 450 and connected directly to output interface 480 through path 430. In this case, digitized RF signals completely bypass blocks 440 and 460 and travel to output interface 480. In another arrangement, digitized signals from A/D block 420 travel on paths 450, but pass through blocks 440 and 460 without being processed. In some embodiments, it may be desirable to turn off blocks 440 and 460 or place them in a low power operating mode to reduce power consumption (e.g., in battery operated disc drives). Although the foregoing illustrates several possible A/D converter arrangements, any other suitable arrangement of resources within DSP 320 may be used as desired If the bypassing of unneeded functionality can be accomplished through programming, no change to existing hardware is needed, although a modification may be needed to drive firmware.

Figure 10:
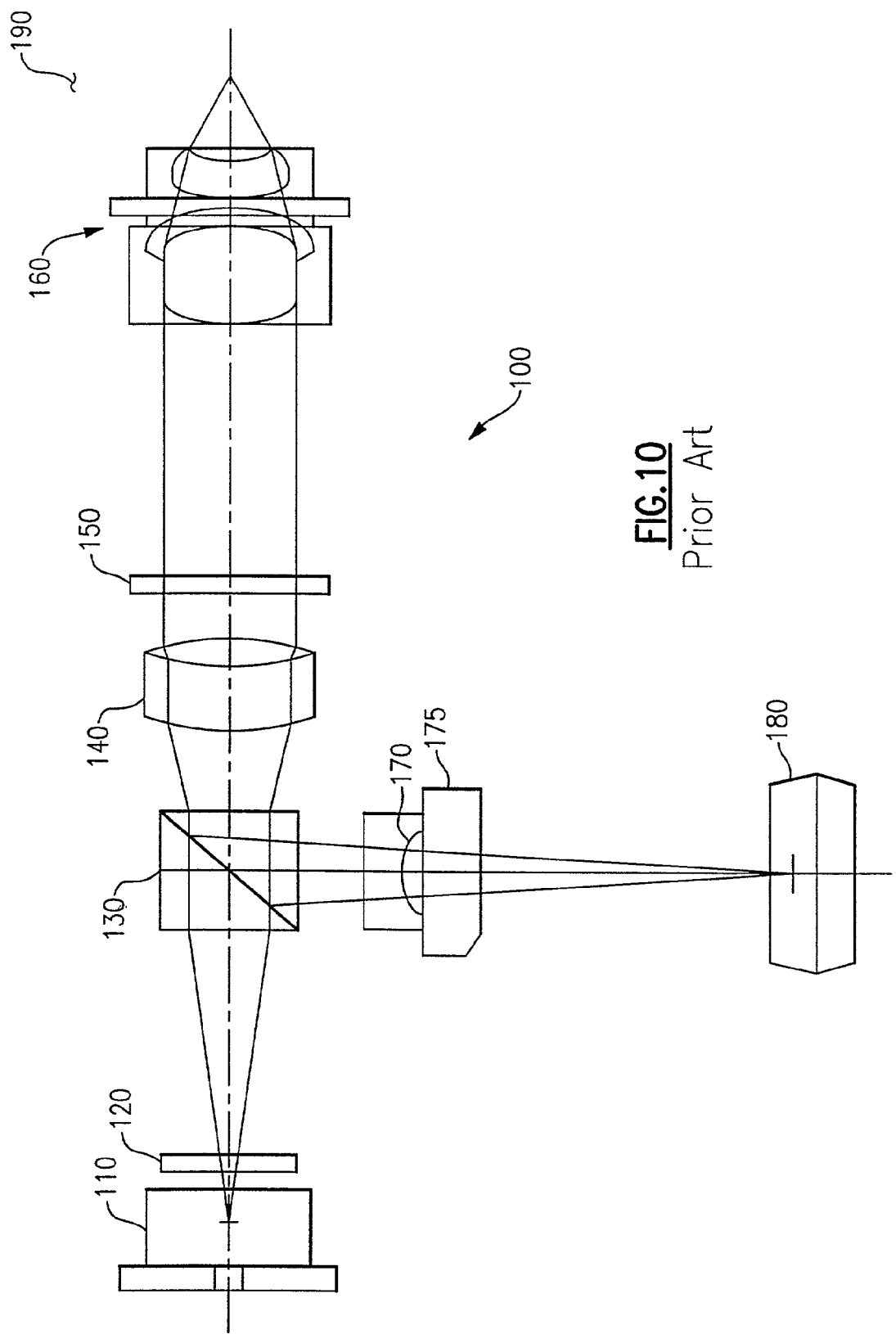
FIG. 10 is a block diagram of a known light projection and detection system.

FIG. 10 shows a conventional single objective assembly 100 designed for multiple (e.g., three-beam) light projection and detection. Light source 110 is placed at a focal point of a collimator lens 140 that normally has a long focal distance. Lens 140 makes the divergent light rays parallel. A monitor diode (not shown) may be used to stabilize the laser's output. Light source 110 may be a laser, LED, or laser diode, although the invention may be implemented on a non-coherent light system as well.

A conventional optical design used for three-beam pickup typically uses two secondary beams for tracking. To generate these beams, light from source 110 passes through diffraction grating 120, which is a screen with slits spaced only a few laser wavelengths apart. As the beam passes through the grating, the light diffracts; when the resulting collection is again focused, it will appear as a single, bright, centered beam with a series of successively less intense beams on either side. It is this diffraction pattern that actually strikes the disc.

A conventional three-beam pickup uses the center beam for reading data and focusing and two secondary beams for tracking only. In this design, the beams are spatially-linked because they are the result of a single diffracted laser beam. A one-beam pickup accomplishes all of these tasks with one beam.

Polarization beam splitter 130 (PBS) passes transmitted light to a disc surface and then directs the reflected light to a photodiode sensor 180. PBS 130 normally includes two prisms with a common 45° face acting as a polarizing prism. Collimator 140 preferably follows PBS 130. The light then passes through a quarter-wavelength plate 150, which is an anisotropic material that rotates the plane of polarization of the light beams. Light that has passed through quarter-wavelength plate 150 and that has been reflected from disc 190 back again through quarter-wavelength plate 150 will be polarized in a plane at right angles to that of the incident light. Because PBS 130 passes light in one plane, (e.g., horizontally polarized) but reflects light on the other plane (e.g., vertically polarized), PBS 130 deflects the reflected beam toward sensor 180 to read the digital data.

The final piece of optics in the optical path to disc 190 is objective lens 160, which is used to focus the beams on the disc data surface, taking into account the refractive index of the polycarbonate substrate of disc 190. Objective lens 160 focuses the light into a convergent cone of light. The convergence is a function of the numerical aperture of the lens.

The data encoded on disc 190 now determines the fate of the laser light. In a regular CD, when the spot strikes a land, the smooth interval between two pits, light is almost totally reflected. When it strikes a pit with a depth of about a quarter wavelength of the light, diffraction and cancellation due to interference cause less light to be reflected. All three intensity modulated light beams return through the objective lens 160, quarter-wavelength plate 150, collimator 140, and PBS 130. Finally, these beams pass through singlet lens 170 and a cylindrical lens 175 en route to photodioide 180.

FIG. 11 shows three light spots which are produced by a typical three-beam optical design incident on an optical disc assembly having pits 90. Laser beam spots 92, 94, and 96 are illustrated as dashed lines on the surface of the optical disc. These beams can be focused on the same surface of the disc as pits 90, or on any other outer surface or inner surface of the disc. These beams can also be focused on different layers of the disc, a "layer" referring to any portion of the disc that has a finite thickness.

In a conventional three-beam optical disc system, detectors a, b, c, and d, as shown in FIG. 4, are configured to detect light reflected from a beam spot 92, as shown in FIG. 11. Also, each of detectors e and f are configured to detect the reflected light from one of beam spots 94 and 96. As mentioned above, this configuration has been implemented such that focus and synchronization information are provided by light reflected at beam spot 92 and the tracking information is provided by light reflected at bears spots 94 and 96.

FIG. 12 shows an investigational feature 98 disposed on a surface of an exemplary optical disc assembly. In this arrangement, beam spot 92 car be used to detect operational structures (e.g., pits) for tracking, focus and synchronization and beam spot 96 can be used simultaneously to primarily one or more investigational features 98. Alternatively, beam spot 94 may be used to detect investigational feature 98, depending on the size and location of investigational feature 98.

Also, if investigational feature 98 is sufficiently large, beam spots 94 and 96 can be used in combination (though not necessarily simultaneously) for detecting a single investigational feature 98. It will be appreciated that a combination of patterns from each of the beam spots can be used to detect the size and position of investigational feature 98. Also, patterns from detectors a, b, c, and d can be combined with patterns from one or both of detectors e and f to determine the size and position of the investigational features.

Thus, operational structures and investigational features can each be detected by different optical paths using a single objective assembly. It will be appreciated that the invention disclosed herein relates to the detection of operational and investigational features and is not limited to an optical disc assembly having a pits and lands format. Rather, the invention can be used with any other format.

Figure 13:
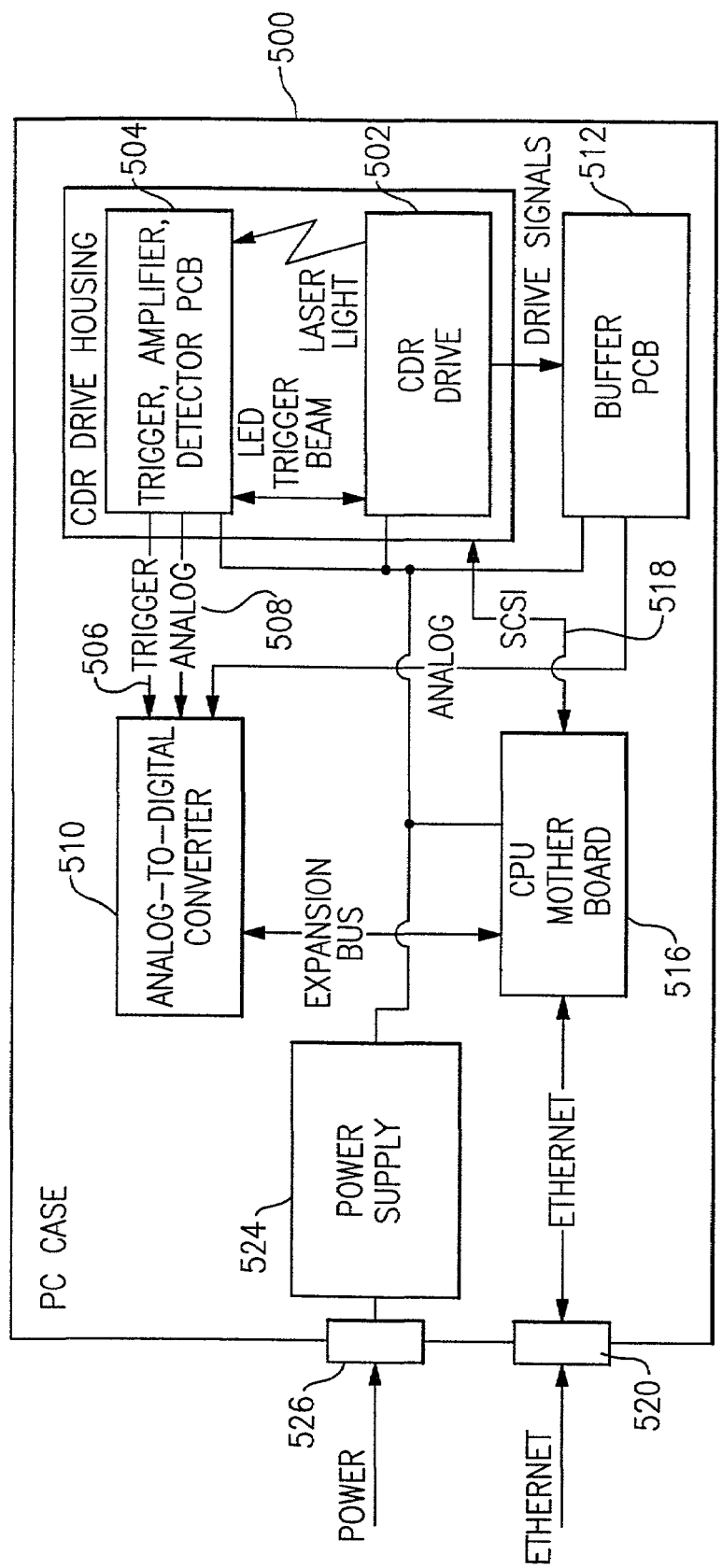
FIG. 13 is a block diagram of an overall drive system according to an embodiment of the present invention.

FIG. 13 shows a block diagram of a computer and a disc drive, such as a CD-R system. The known CD-R system can include a laser and detection circuitry as shown in FIGS. 4 and 6 for detecting reflected light. According to an embodiment of the present invention, additional CD-R drive functionality. including a detector for transmissive light, and a trigger detector, and processing circuitry, preferably on a single printed circuit board (PCB) 504, is added to the CD-R drive housing. This functionality thus detects transmitted light, trigger marks, and amplifies an analog data signal based on the detected transmitted light. These additions are preferably made so that no change is needed to existing CD-R electrinics, and thus a conventional optical disc drive may be modified prior to initial shipment or retrofitted with the additional functionality without the need to alter the CD-R hardware. While using existing functionality has advantages, any changes made to a disc reader could be done by making changes to or modifying an existing reader A trigger signal 506, indicating whether a trigger is identified, and an analog data signal 508 are both provided to an analog-to-digital converter (ADC) 510. ADC 510 collects data when the trigger signal indicates detection of a trigger mark, and does not collect data when a trigger mark is not detected. Alternatively, the trigger signal could be provided in the operational data, such that encoded information on the disc indicates the location of the investigational features. Alternatively, the entire disc is scanned to read all the data on the disc, but only data following a predefined set of data. In this way, all the data on the disc can initially be read into memory, but then the data other than that following the software trigger can be discarded.

Optionally, a second trigger mark can be provided as well. This second mark can be useful to distinguish from among multiple target zones and better enables the user to look at a particular zone rather than all the zones. One trigger mark and one trigger mark detector must be located at a different radius than all of the others.

ADC 510 also receives analog drive signals via a buffer PCB 512 which receives its input signals from CD-R drive 502. A CPU motherboard 516 communicates with the CDR drive 502 over a small computer systems interface (SCSI) 518 and receives data through an expansion bus from ADC 510. CPU motherboard 516 has an Ethernet connection that allows this data to be offloaded for further processing.

A power supply 524 receives a power input 526 and provides the power to the motherboard 516 as well as to the other components in the CDR drive housing 500 and in the PC.

The data can be processed as it is collected in a real-time manner, or may be stored and post processed by other computers, potentially reducing the complexity of the system.

The trigger, amplifier, detector (TAD) PCB 504 is preferably constructed in such a manner that it can be provided into a conventional optical drive of the type that can be used in a drive bay in a computer. One suitable drive used particularly for development purposes is the Plextor model 8220 CD-R drive. While a CD or DVD can be used, a CD-R drive has several useful aspects. Because the CD-R drive allows reading and writing functions, the laser can operate over a higher range of power levels. This functionality of using higher power can be useful for certain types of investigational features. Another useful aspect of a CD-R is that it has the ability to write onto a disc and therefore can be used to write results back onto a disc. This allows results to be saved back onto the disc for later use and to remain with the disc.

Figure 14:
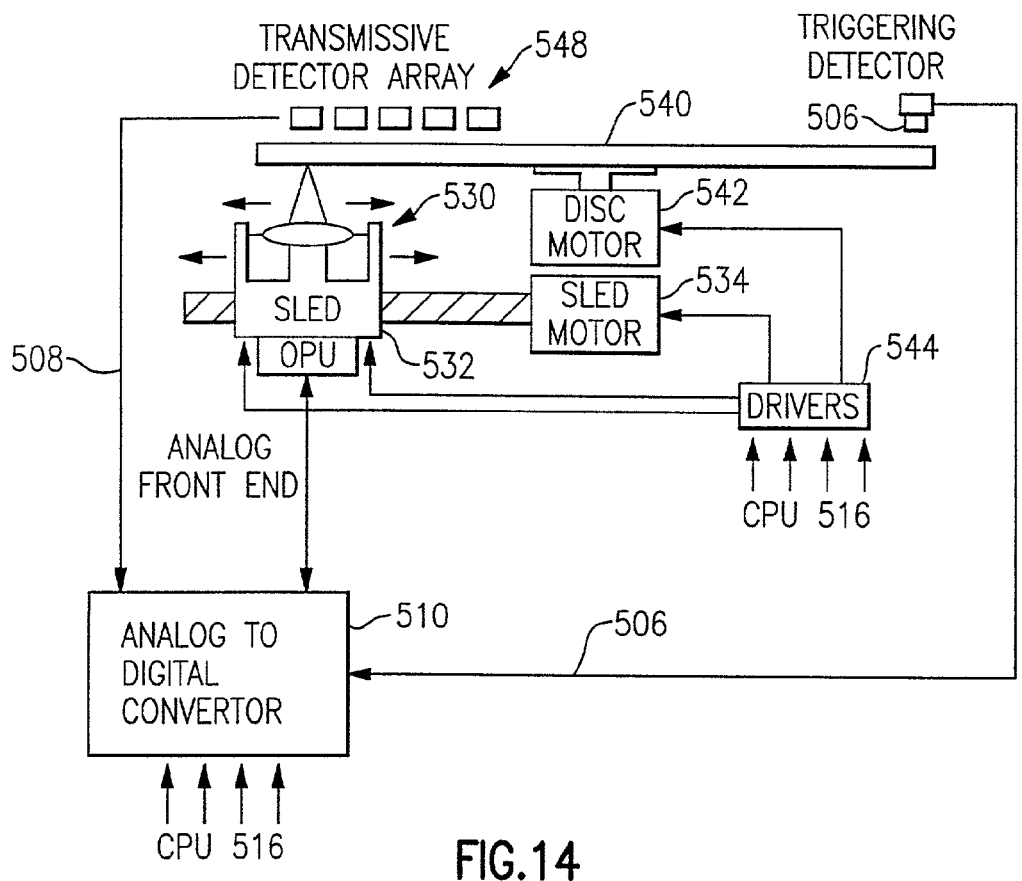
FIG. 14 is a part pictorial part block diagram showing a disc and a reading system.

FIG. 14 is a block diagram that illustrates in more detail the inter-relationship between TAD PCB 504 and the disc drive mechanisms. As it is shown here, optical components 530 are mounted on a sled 532 that is driven by a sled motor 534, and the disc is driven by a disc motor 542. These two motors are driven by drivers 544 that receive signals from CPU 516 and may be conventional and known. Data from the optical components 530, triggering detector signal 506, and signals 508 from a transmissive detector or detector array 548 are all provided to PCB 504. The detector for processing the signal from the transmitted or reflected beam of light may be a single detector element or an array of multiple elements arranged radially or circumferentially, and may be placed on the opposite side of the disc from the laser, and may be mounted directly on the PCB or separately.

Figure 15:
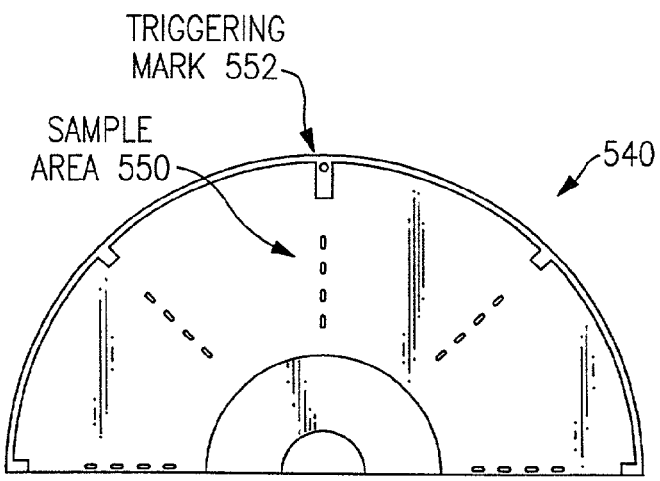
FIG. 15 is a plan view of a disc showing assay regions and a hardware trigger.

Referring also to FIG. 15, which is a plan view of a disc showing sample areas and triggering mark, the hardware trigger is preferably disposed at an outer periphery of the disc, and preferably is in a radial line with sample areas 550. The trigger indicates that the light beam is in a radial line with sample areas 550 and allows the ADC to process data. This trigger helps to reduce the amount of data that is collected.

Referring to FIG. 13, the trigger functionality, amplification circuitry, and transmissive light detection are preferably performed on a single PCB and preferably have a size, shape, and configuration that allow it to be incorporated into existing commercial disc drives.

The ADC may be on a sampling card that allows for very high speed conversion. One usable card is the Ultrad AD 1280 DX, which has two 12-bit A/D converters sampling up to forty million samples per second.

There are advantages to making changes to the disc drive that provide the least amount of disruption to conventional drives. For this reason, it can be desirable to use a disc that is transmissive. In other words, the disc is reflective enough for the operational data to be seen by the active electronics and normal drive functioning to occur. Yet, the light passes through the disc to a detector on the other side of the disc. In this manner, the investigational features can be detected without it being necessary to alter the detection circuitry for reflected light. The reflected light may still be used to read encoded data.

One way to cause fewer changes is to provide a board that will fit within the space of a conventional housing and which is over the disc on the opposite side of where the laser is situated.

Figure 16:
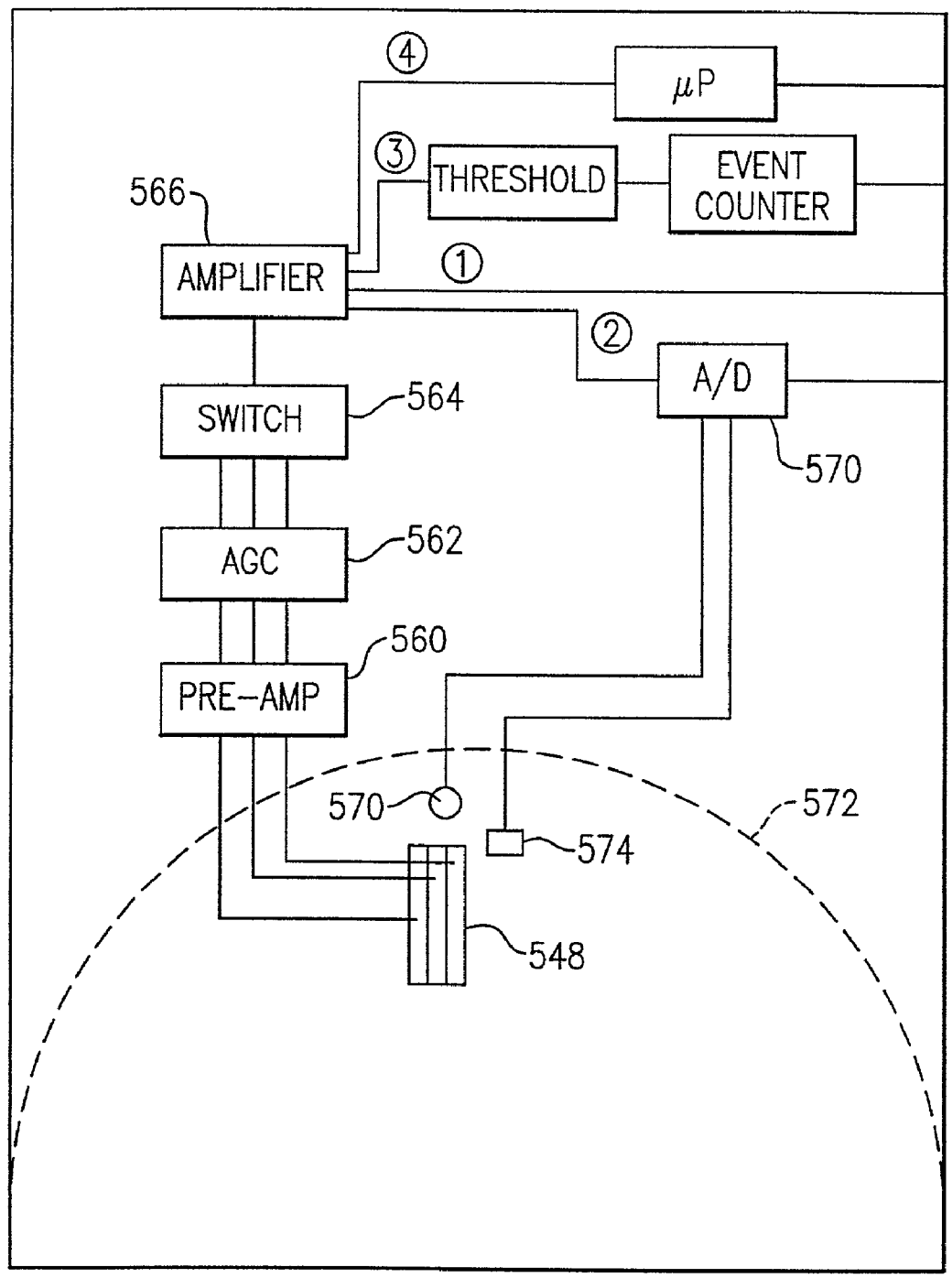
FIG. 16 is a block diagram of a board with functionality including a trigger, an amplifier, and detection circuitry.

Referring to FIG. 16, PCB 504 can include a transmissive detector 548 located over the viewing regions. This detector can be a single detector, an array arranged with different segments oriented radially, or an array with multiple segments oriented circumferentially with multiple detectors arranged along different radii. The detector receives signals and provides them to a preamplifier 560, automatic gain control 562, switch 564, and amplifier 566 to produce a signal on the order of 3 volts.

Triggering light source and detector 570 can be provided on PCB 504. This hardware would include a light source and a detector positioned to detect trigger marks, preferably at the periphery of the disc 572. The trigger signal is provided to the ADC such that the ADC only collects and stores data when the triggering signal indicates that the system has detected a trigger, thereby saving on the processing that is required and the data that is stored. A second trigger light source and detector 574 can be provided in order to help distinguish from among a plurality of trigger marks. In this case, both trigger signals are provided to a trigger control circuit. The trigger control circuit passes trigger signals to collect and retain data from the desired sample areas on to the ADC.

As an alternative to this hardware triggering, a software trigger could be used.

Analog switch 564 can be used when the data detector is an array with multiple elements. There can be multiple detector elements that perform some of the types of refracted light combinations. For example, sums and differences can be used. If desirable, the switch can also be coupled to the detection elements that are under the disc for detecting reflected light. This could allow the system to obtain a differential between the top and bottom detection.

Additional processing and counting functionality can be provided on the PCB in order to move the processing from the ADC 510 and external computer or effectively to replace the ADC and computer to provide that more processing occur on the PCB. In the case of the test for CD4/CD8, for example, one methodology that is used is to count white blood cells in a target region. As the laser light is scanned over the assay region, the detector will detect no light at the edge of a blood cell, and will detect full light when centered on a blood cell. As the beam is scanned, it therefore creates a series of high and low signals indicating where a cell is detected. Processing functionality can be added to the card to include threshold crossing circuitry and a counter. Such processing is less complex than that that may be used for other tests. Each of these types of circuits is generally known. Depending on the type of test that is used (the CD4/CD8 being one example), the processing system may need to count hundreds or up to tens of thousands of features in the assay region. In addition, a microprocessor could also be added to the card.

By providing additional processing and/or counting functionality onto the card, the results from scanning the sample can be provided directly from the card for direct use, such as to a USB port or through an Ethernet port. By using Ethernet, data can be provided from a web server such that users can access data with a web browser.

The PCB can also include a temperature sensor and other sensors (not shown) that may be useful for testing. In the case of temperature, a test, may use a level of darkness in a material to indicate the relative presence of some material. For example, a glucose test may rely on the darkness of a fluid, and thus colorimetry is used. For tests for which temperature is a factor, the temperature sensor can be used and can be a factor used in the processing of the data.

Another detector that can be provided is a simple barcode reader that can be used if barcodes are provided on the disc for identification purposes.

The automatic gain control (AGC) 562, and also automatic level control (ALC), makes sure that the full dynamic range is used, and thus the signals may range, for example, from 0 to 3 volts. ALC is used to define a center of the signal, such as 1.5 volts if the range is 0 to 3 volts. The result of the amplification, ACG, and ALC is that the output can be processed through a threshold circuit and provide consistent results.

So far, this application has described one method in which the processing of reflective light intensity is utilized to provide for the detection of investigational features. This application has also described a system and method by which hardware can be added to a conventional optical disc drive in order to use light that is transmitted through the disc. Another approach for modifying conventional disc drive, preferably without the need to modify the electronics or hardware, is to use firmware modifications to monitor known signals within the disc drive. The value of the AGC can be useful as an measuring tool. The AGC functionality tries to ensure that the analog output signal has a consistent range. If the disc drive is used to read binary data, only a high value and a low value are needed. In the case of investigational features, however, values may be desirable over a continuum of ranges. The AGC is high where the signal level is low, and vice versa. The AGC can thus be used as a signal that is representative of the light that is received by the detector, and therefore can be used for measurement and detecting changes in an investigational feature.

A conventional optical disc reader is generally provided to a user to allow the user to play a disc with little ability to control the parameters of the reading, rotating, and data processing; for the most part, users of commercial CD and DVD players would not need such abilities (and likely would not want to have to set parameters).

The changes set out below, for the most part, are ones that do not require hardware change, and for the most part are typical of modifications that may be made in disc and drive analysis systems in which various parameters of discs and drives are measured and refined. In the case of a regular CD or DVD commercial product, however, these changes would generally not be made and would be unnecessary.

These changes can be made in firmware, and generally can be made by post-purchase software modification. In other words, the programming could be provided to a user on a disc or by download, and thus no hardware changes are required. These programming changes could be read from a disc, e.g., at startup, and used to modify the ability to control the operation of the drive.

The changes can include one, all, or some combination of the following capabilities:

1. Wobble groove playback and random access on a wobble groove: rather than needing to start from the beginning of a disc; this change allows the drive to go to an LBA (or an address by some other mode) and play forward from there.

2. Poll the laser monitor value: allows reading of the value of the laser power detected by the laser power monitor detector in the optical pickup unit.

3. Poll and set the laser power read/play value: monitor and set the power command value to the laser to allow a range of values.

4. Poll the automatic gain control (AGC): ability to get the value of the AGC. The gain is controlled to make sure that the detected signals have a consistent amplitude. The amount of gain therefore is an inverse indicator of the signal intensity. Consequently, the signal can be used for detection and measurement.

5. Poll the tracking automatic gain control value.

6. Monitor the C1 and/or P1 decoder activity at a port; this change and the one in (7) below, relate to the ability to monitor types of errors to see the error counts; this is useful because the errors could be useful information for detecting where an investigational feature is. A conventional drive detects gaps in the encoded data as an error.

7. Monitor the C2 and/or PO decoder activity at a port: see (6) above.

8. Initialize and track operational features on a disc independent of encoded logic: This refers to the ability to control the laser position and control the speed of the disc independent of the data. This functionality allows a user to send a command to keep the drive motor spinning without its operational functions of focus, tracking, and synchronization.

9. Initialize the drive with a specific speed and laser read power: a drive typically has a start-up speed and laser power that is not changed by a user; this change allows these values to be set and changed by the user. Because a liquid is being provided to the disc, it may be desirable not to spin the disc as soon as it is provided into the disc drive. In a typical disc drive system, however, the disc immediately starts to spin to get a focal point, get synchronization information, and find a table of contents; typically if these are not found, the disc drive will open up and shut down. As indicated above, because liquid is provided, it may be desirable to not spin the disc as soon as it is provided into the disc drive but to wait for further instructions. This change also relates to the change set out in No. 15 below.

10. Stream the main and sub-channel data in all areas of the disc including lead-in and lead-out: allows more portions of the disc to have data.

11. Push raw-EFM (eight-fourteen modulation) value to a port or secondary port: allows the user to see 14-bit data before it is translated to 8-bit values. This functionality allows the user to more clearly know exactly what is on the disc. Like No. 10 above, this change allows additional areas on the disc to be used.

12. Push buffered, DC coupled signals, such as TE, FE, and HF, to an external port; relates to the ability to provide these values to a port to be used, where generally they are used for internal purposes (see FIGS. 4 and 6).

13. Decode and poll values collected from the power calibration area (PCA) and program memory area (PMA) at initialization. Allows additional information to be collected.

14. Pause playback of a disc and open the tracking servo to monitor the open loop tracking signal: allows the user to monitor the eccentricity of the disc. A disc generally had some eccentricity and therefore the tracking signal will have a periodic form as the disc is rotated. The eccentricity of the disc arises from nonperfect processing of the disc. The tracking signal is thus a reflection of the eccentricity which produces a periodic signal that is a reflection of the eccentricity. If there is a change in reflectivity in one area, such as due to the presence of an investigational feature, the tracking signal will reflect this change in reflectivity.

15. Set Ghost initialization logic: As indicated in No. 9 above, when a disc is put into a disc drive, it typically starts up and one of the initial functions is to find a table of contents. If the disc is not spun initially, there will not be a table of contents found. Accordingly, this change allows the user to provide to the disc drive controller a table of contents to effectively trick the disc drive into thinking that it has read the table of contents from the disc.

16. Interactively turn off tracking function.

17. Control and monitor the focusing offset with or without the tracking function. The focus offset changes the size of the laser spot, and thereby changes the amount of energy. It may be desirable to provide heating to the disc or a region of the disc, and therefore the ability to control the focus offset can allow the user to control the heating.

18. Switch layers on a DVD.
19. Monitor value changes at the switching port:
20. Read a CD or CD-RW with a DVD laser: the DVD laser is at a lower wavelength, which can be useful for imaging and for fluorescent detection. Devices that have the ability to read CD and DVD are generally provided with two lasers, one for each mode.
21. Track a wobble groove (1.2 mm) at any frequency with a DVD laser.
22. Monitor the value of a buffered DPD signal: The differential phase detection (DPD) signal is a DVD signal used for tracking, and thus this corresponds to previously discussed ability to monitor the tracking signal.

These changes can primarily be made in a firmware, which is generally more preferable and allows retrofitting a commercial product for use in detecting investigational features, but could alternatively be done in hardware.

Having described certain embodiments, it should become apparent that modifications can be made without departing from the scope of the claims as set out below. For example, the terms over and under are used for reference purposes and not absolute positioning. The disc could be read with reflected light from the top or the drive could be on its side.

What is claimed is:

1. A method for a disc drive system to read a disc having target zones, at least one of which has an investigational feature, the method comprising:
   directing a light source to the disc;
   detecting light reflected from the disc;
   detecting light transmitted through the disc;
   providing a detector signal representing the detected transmitted light;
   processing the detector signal with processing circuitry; and
   detecting a trigger indicating the location of a target zone and providing a trigger signal when the trigger is detected;
   the trigger signal causing the processing circuitry to disregard the detector signal when the trigger signal does not indicate the target zone, and processing the detector signal when the trigger signal indicates the target zone.

2. The method of claim 1, wherein the trigger includes an encoded data pattern in the disc.

3. The method of claim 1, wherein the trigger includes a physical detectable mark on the disc.

4. The method of claim 3, wherein detecting a trigger includes directing a second light source to the disc and detecting light reflected from or transmitted to the disc at the mark.

5. The method of claim 3, further comprising a second physical detectable mark on the disc for identifying a second target zone, and a third physical detectable mark on the disc detectable for distinguishing the first mark from the second mark.

6. The method of claim 2, wherein the processing circuitry does not collect data when the trigger signal does not indicate a target zone.

7. The method of claim 2, wherein the processing circuitry deleted collected data when the trigger signal does not indicate a target zone.

8. A method for a disc drive system to read a disc having target zones, at least one of which has an investigational feature, the method comprising:
   directing a light source to the disc;
   detecting light reflected from the disc;
   processing the detector signal with processing circuitry; and
   detecting a trigger indicating the location of a target zone and providing a trigger signal when the trigger is detected;
   the trigger signal causing the processing circuitry to process in one way if the trigger signal does not indicates the target zone, and in a different way if the trigger signal indicates the target zone.

9. The method of claim 8, wherein the detected light may represent encoded information or an investigational feature.

10. A method for use by a disc drive system for reading a disc with an investigational feature and including accessing a desired location in a wobble groove and scanning forward from that location.

11. A control method for an optical disc drive for general use and not as a dedicated disc analyzer, a method of causing the disc drive not to spin when an optical disc with an investigational feature is inserted into the disc drive system.

12. The method of claim 11, wherein the drive does not read the table of contents for the disc, the method further providing a table of contents for the disc in a ghost file sent to the drive.

* * * * *